United States Patent
Inoue et al.

(10) Patent No.: US 8,653,269 B2
(45) Date of Patent: Feb. 18, 2014

(54) PROCESS FOR PREPARATION OF T-BUTOXYCARBONYLAMINE COMPOUNDS

(75) Inventors: Hiroki Inoue, Takaoka (JP); Kaoru Noda, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/583,095

(22) PCT Filed: Mar. 8, 2011

(86) PCT No.: PCT/JP2011/055380
§ 371 (c)(1),
(2), (4) Date: Sep. 6, 2012

(87) PCT Pub. No.: WO2011/111705
PCT Pub. Date: Sep. 15, 2011

(65) Prior Publication Data
US 2013/0005981 A1 Jan. 3, 2013

(30) Foreign Application Priority Data
Mar. 12, 2010 (JP) .................. 2010-056717

(51) Int. Cl.
*C07C 211/00* (2006.01)
(52) U.S. Cl.
USPC .......................................................... 546/1
(58) Field of Classification Search
USPC .......................................................... 564/1
See application file for complete search history.

(56) References Cited

U.S. PATENT DOCUMENTS

2008/0108814 A1  5/2008  Silverman et al.

FOREIGN PATENT DOCUMENTS

| CN | 101103012 A | 1/2008 |
| EP | 1659113 A1 | 5/2006 |
| WO | 2005/023814 | 3/2005 |
| WO | 2008/113469 A2 | 9/2008 |
| WO | 2009/050234 A1 | 4/2009 |

OTHER PUBLICATIONS

Jahani et al (Monatsh Chem (2011) 142:1035-1043.*
International Search Report issued for PCT/JP2011/055380, dated Jun. 21, 2011, 3 pages (with English translation).
Pothukanuri, Srinivasu, et al., "Expanding the Scope and Orthogonality of PNA Synthesis", Eur. J. Org. Chem., 2008, pp. 3141-3148.
McKay, Frank C., et al., "New Amine-masking Groups for Peptide Synthesis", J. Am. Chem. Soc., 1957, vol. 79, pp. 4686-4690.
Mormeneo, David, et al., "A practical synthesis of carbamates using an 'in-situ' generated polymer-supported chlorofonnate", Tetrahedron Letters, 2004, vol. 45, pp. 6831-683.
Yajima, Karuaki, et al., "A Convenient Method for the Preparation of *tert*-Butyl Azidoformate", Chem. Pharm. Bull., 1968, vol. 16, No. 1, pp. 182-184.
Office Action issued in the corresponding CN Appln. No. 201180013214.7, dated Aug. 8, 2013, 20 pages (with English translation).

* cited by examiner

*Primary Examiner* — Nizal Chandrakumar
(74) *Attorney, Agent, or Firm* — Kenyon & Kenyon, LLP

(57) ABSTRACT

Provided is a process for the preparation of t-butoxycarbonylamine compounds, which comprises using phosgene or a phosgene equivalent, t-butanol, and an organic base. Even when applied to a primary or secondary amine compound having low nucleophilicity, the process enables highly selective preparation of a t-butoxycarbonylamine compound at a low cost. In the process, a t-butoxycarbonylamine compound is prepared using: phosgene or a phosgene equivalent; t-butanol; an organic base; and either a primary or secondary amine compound or a primary or secondary ammonium salt.

14 Claims, No Drawings

PROCESS FOR PREPARATION OF T-BUTOXYCARBONYLAMINE COMPOUNDS

TECHNICAL FIELD

The present invention relates to a process for preparation of t-butoxycarbonylamine compounds. More particularly, the present invention relates to a process for preparation of t-butoxycarbonylamine compounds using phosgene or a phosgene equivalent, t-butanol and an organic base both inexpensively and with high selectivity even if applied to lowly nucleophilic primary or secondary amine compounds.

The present application claims priority on the basis of Japanese Patent Application No. 2010-056717, filed in Japan on Mar. 12, 2010, the contents of which are incorporated herein by reference.

BACKGROUND ART

A known process for introducing a t-butoxycarbonyl (hereinafter, also referred as "Boc") group into a primary or secondary amino group consists of reacting the primary or secondary amine compound with phosgene or a phosgene equivalent in the presence of an organic base, followed by reacting with t-butanol. Since the phosgene or phosgene equivalent used in the reaction can be acquired inexpensively, the process is industrially useful.

Patent Document 1, for example, describes the obtaining of a Boc compound represented by the following formula (C) by adding triethylamine to the aniline compound represented by formula (A) in the presence of triphosgene and in a toluene solvent to convert to the isocyanate compound represented by formula (B), followed by adding t-butanol and triethylamine to the toluene solution of the isocyanate compound represented by formula (B).

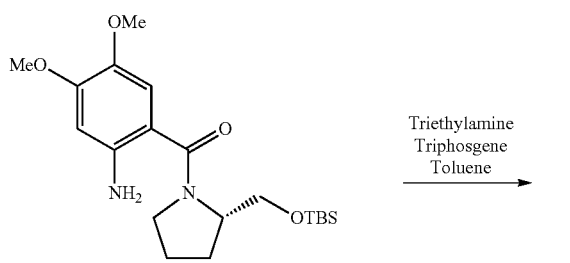

(A)

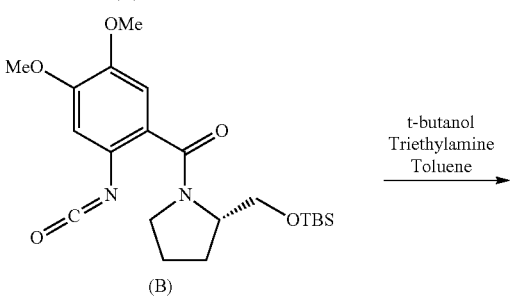

(B)

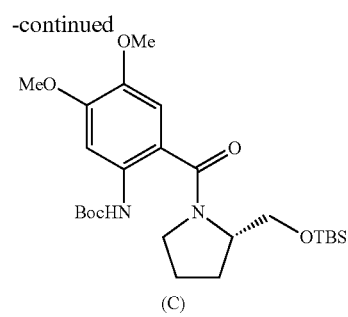

(C)

Non-Patent Document 1 discloses the obtaining of a target Boc compound represented by the following formula (E) at a yield of 87% by adding triphosgene to a tetrahydrofuran solution of a compound represented by formula (D) at 0° C., followed by adding diisopropylethylamine and finally adding t-butanol.

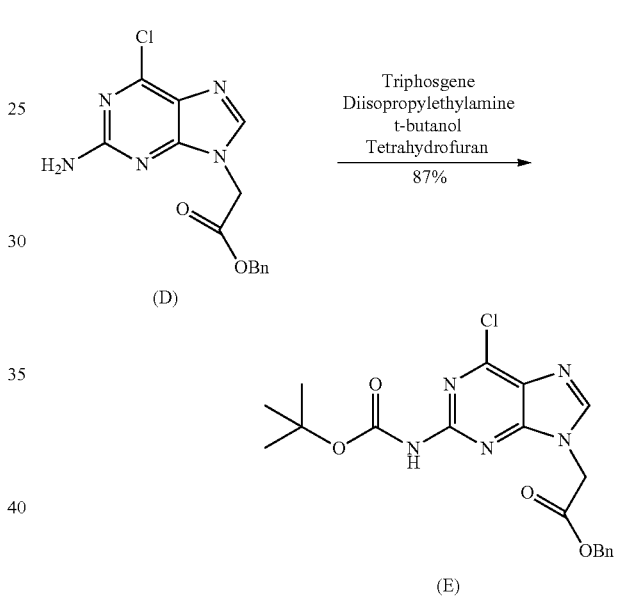

PRIOR ART DOCUMENTS

Patent Documents

Patent Document 1: International Publication No. WO 2005/23814

Non-Patent Documents

Non-Patent Document 1: European Journal of Organic Chemistry, 2008, pp. 3141-3148

DISCLOSURE OF THE INVENTION

Problems to be Solved by the Invention

When the process described in Patent Document 1 or Non-Patent Document 1, namely a process for reacting phosgene or a phosgene equivalent with a primary or secondary amine compound in the presence of an organic base followed by reacting with t-butanol, is applied to a compound having a lowly nucleophilic amino group (for example, such as a 2-aminopyridine derivative), compounds having urea bonds ends up being formed secondarily in large amounts, thereby causing a decrease in yield of the Boc compound.

Therefore, an object of the present invention is to provide a process for producing t-butoxycarbonylamine compounds by using phosgene or a phosgene equivalent, t-butanol and an organic base both inexpensively and with high selectivity even if applied to a lowly nucleophilic primary or secondary amine compound.

Means for Solving the Problems

As a result of conducting extensive studies to achieve the aforementioned object, the inventor of the present invention found that production of compounds having urea bonds as a by-product can be inhibited and t-butoxycarbonylamine compounds can be obtained at high yield by reacting phosgene or a phosgene equivalent, t-butanol an organic base and a primary or secondary amine compound or primary or secondary ammonium salt under certain conditions. The present invention was completed as a result of conducting further studies based on this finding.

Namely, the present invention includes the aspects indicated below.

(1) A process for producing t-butoxycarbonylamine compounds, comprising an use of phosgene or a phosgene equivalent, t-butanol, an organic base and a primary or secondary amine compound or primary or secondary ammonium salt, which includes any one of following processes (a) to (f):
  (a) a process comprising an addition of a solution containing a primary or secondary amine compound and an organic base to a solution containing phosgene or a phosgene equivalent and t-butanol;
  (b) a process comprising an addition of a solution containing a primary or secondary amine compound, an organic base and t-butanol to a solution containing phosgene or a phosgene equivalent;
  (c) a process comprising a substantially simultaneous addition of a solution containing a primary or secondary amine compound, a solution containing an organic base and a solution containing phosgene or a phosgene equivalent to a solution containing t-butanol;
  (d) a process comprising an addition of a solution containing a primary or secondary amine compound and a solution containing an organic base to a solution containing t-butanol while blowing in phosgene gas;
  (e) a process comprising an addition of a solution containing t-butanol, a primary or secondary amine compound and an organic base to a reaction solution while blowing in phosgene gas; and,
  (f) a process comprising an addition of an organic base to a solution containing phosgene or a phosgene equivalent, t-butanol and a primary or secondary ammonium salt.
(2) The process for producing t-butoxycarbonylamine compounds described in (1), wherein the primary or secondary ammonium salt is a primary or secondary ammonium hydrochloride.
(3) The process for producing t-butoxycarbonylamine compounds described in (1) or (2), wherein the reaction is carried out in an organic solvent.
(4) The process for producing t-butoxycarbonylamine compounds described in (3), wherein the organic solvent is at least one type selected from a group consisting of ethyl acetate, chlorobenzene and chloroform.
(5) The process for producing t-butoxycarbonylamine compounds described in any one of (1) to (4), wherein the primary or secondary amine compound is an amine compound having an N-substituted heteroaromatic hydrocarbon group.
(6) The process for producing t-butoxycarbonylamine compounds described in (5), wherein the amine compound having an N-substituted heteroaromatic hydrocarbon group is a 2-aminopyridine derivative.
(7) The process for producing t-butoxycarbonylamine compounds described in any one of (1) to (6), wherein the organic base is a tertiary amine.
(8) The process for producing t-butoxycarbonylamine compounds described in (7), wherein the tertiary amine is N,N-diisopropylethylamine or triethylamine.
(9) The process for producing t-butoxycarbonylamine compounds described in any one of (1) to (8), wherein a temperature from start of the reaction to completion of the reaction is 40° C. or lower.

Effects of the Invention

According to the production process of the present invention, a Boc group can be introduced into a primary or secondary amine compound inexpensively while inhibiting the formation of by-products.

BEST MODE FOR CARRYING OUT THE INVENTION

As described above, the method for producing t-butoxycarbonylamine compounds of the present invention includes reacting phosgene or a phosgene equivalent, t-butanol, an organic base and a primary or secondary amine compound or a primary or secondary ammonium salt under certain conditions.

The primary amine compound used in the present invention is a compound represented by $NH_2R^0$, while the secondary amine compound is a compound represented by $NHR'R^2$. There are no particular limitations on $R^0$, $R^1$ and $R^2$, and examples thereof include an alkyl group, cycloalkyl group, aryl group, heteroaryl group and aralkyl group. Among these, an aryl group or heteroaryl group is preferable.

Examples of the primary or secondary amine compound used in the present invention include aliphatic amine compounds such as methylamine, dimethylamine, ethylamine, diethylamine, propylamine, cyclohexylamine, piperidine, pyrrolidine and amantadine; aromatic amine compounds such as aniline, o-toluidine, p-toluidine, catecholamine or phenethylamine, and heterocyclic group-containing amine compounds such as quinoline amines, pyridine amines or pyrrole amines. Among these, compounds having a lowly nucleophilic amino group are suitable, amine compounds having an N-substituted heteroaromatic hydrocarbon group are preferable, and 2-aminopyridine derivatives are particularly preferable in the present invention. Among 2-aminopyridine derivatives, a compound represented by the following formula (I) is preferable:

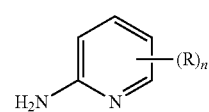

[1]

(wherein, R represents a C1-6 alkyl group, C1-6 haloalkyl group, C2-6 alkenyl group, C2-6 alkynyl group, C3-6 cycloalkyl group, C1-6 alkoxy group, C1-6 alkoxy C1-6 alkyl group, C1-6 alkylthio group, amino group, mono- or di-C1-6 alkylamino group, C1-6 alkylcarbonyloxy group, aryl group, heteroaryl group, aralkyl group, heteroaralkyl group, aralkyloxy group, heteroaralkyloxy group, nitro group, cyano group, hydroxy group, halogen atom, —OSO$_2$CF$_3$, —OSO$_2$Me, —OSO$_2$Ph, —OSO$_2$Ph-p-Me or group represented by formula [a]:

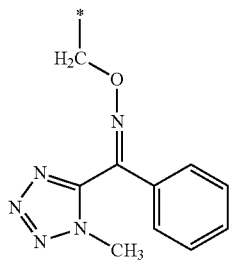

(wherein, * represents the bonding site to the pyridine ring of formula [1]), and n represents the substitution number of R that is an integer of 0 to 4, and R may be the same or different when n is 2 or more).

A C1-6 alkyl group is a saturated aliphatic hydrocarbon group composed of 1 to 6 carbon atoms. The C1-6 alkyl group may be linear or branched. Specific examples include a methyl group, ethyl group, n-propyl group, isopropyl group, n-butyl group, isobutyl group, s-butyl group, t-butyl group, n-pentyl group and hexyl group.

A C1-6 haloalkyl group is a group in which a hydrogen atom of a C1-6 alkyl group is substituted with a halogen atom. Specific examples include a fluoromethyl group, chloromethyl group, bromomethyl group, difluoromethyl group, dichloromethyl group, dibromomethyl group, trifluoromethyl group, trichloromethyl group, tribromomethyl group, 2,2,2-trifluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethylethyl group, perfluorohexyl group, perchlorohexyl group and 2,4,6-trichlorohexyl group.

A C2-C6 alkenyl group is an unsaturated hydrocarbon group composed of 2 to 6 carbon atoms that has at least one carbon-carbon double bond. The alkenyl group may be linear or branched. Specific examples include a vinyl group, 1-propenyl group, allyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group and 5-hexenyl group.

A C2-6 alkynyl group is an unsaturated hydrocarbon group composed of 2 to 6 carbon atoms that has at least one carbon-carbon triple bond. The alkynyl group may be linear or branched. Specific examples include an ethynyl group, 1-propynyl group, propargyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group and 1,1-dimethyl-2-butynyl group.

A C3-6 cycloalkyl group is an alkyl group composed of 3 to 6 carbon atoms that has a ring moiety. Examples of the cycloalkyl group include a cyclopropyl group, cyclobutyl group, cyclopentyl group, cyclohexyl group, cyclopropylmethyl group, 2-cyclopropylethyl group and cyclopentylmethyl group.

A C1-6 alkoxy group is a group in which a C1-6 alkyl group is bonded to an oxygen atom. Examples of the C1-6 alkoxy group include a methoxy group, ethoxy group, n-propoxy group, i-propoxy group, n-butoxy group, i-butoxy group, s-butoxy group, t-butoxy group, n-pentyloxy group, 1-ethylpropoxy group, n-hexyloxy group, isohexyloxy group, 4-methylpentoxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group and 2-ethylbutoxy group.

A C1-6 alkylthio group is a group in which a C1-6 alkyl group is bonded to a sulfur atom. Examples the C1-6 alkylthio group include a methylthio group, ethylthio group, n-propylthio group, i-propylthio group, n-butylthio group, t-butylthio group, pentylthio group, isopentylthio group, 2-methylbutylthio group, neopentylthio group, 1-ethylpropylthio group, hexylthio group, isohexylthio group, 4-methylpentylthio group, 3-methylpentylthio group, 2-methylpentylthio group, 1-methylpentylthio group, 3,3-dimethylbutylthio group, 2,2-dimethylbutylthio group, 1,1-dimethylbutylthio group, 1,2-dimethylbutylthio group, 1,3-dimethylbutylthio group, 2,3-dimethylbutylthio group and 2-ethylbutylthio group.

Examples of an amino group or mono- or di-C1-6 alkylamino group include an unsubstituted amino group, methylamino group, ethylamino group, dimethylamino group and diethylamino group.

Examples of a C1-6 alkylcarbonyloxy group include an acetyloxy group, propionyloxy group, n-propylcarbonyloxy group, i-propylcarbonyloxy group, n-butylcarbonyloxy group, i-butylcarbonyloxy group and pivaloyloxy group.

An aryl group is a monocyclic or polycyclic aryl group. In a polycyclic aryl group, as long as at least one of the rings is an aromatic ring, the remaining rings may be saturated alicyclic rings, unsaturated alicyclic rings or aromatic rings. Examples of the aryl group include a phenyl group, 1-naphthyl group, 2-naphthyl group, azulenyl group, indenyl group, indanyl group or tetralinyl group. Among these, a phenyl group is preferable.

A heteroaryl group is an aryl group having 1 to 3 nitrogen atoms, oxygen atoms or sulfur atoms. Examples of heteroaryl groups include a furyl group, thienyl group, pyrrolyl group, oxazolyl group, pyridyl group, pyrazyl group, pyrimidyl group, quinolinyl group and carbazolyl group. Among these, 5- to 10-membered heteroaryl groups are preferable.

An aralkyl group is a group in which an aryl group is bonded to an alkyl group. Examples of aralkyl groups include a benzyl group, phenethyl group, 3-phenylpropyl group, 1-naphthylmethyl group and 2-naphthylmethyl group. Among these, C6-10 aryl C1-6 alkyl groups are preferable.

A heteroaralkyl group is a group in which a heteroaryl group is bonded to an alkyl group. Examples of heteroaralkyl groups include a 2-pyridylmethyl group, 3-pyridylmethyl group, 4-pyridylmethyl group, 2-(2-pyridyl)ethyl group, 2-(3-pyridyl)ethyl group, 2-(4-pyridyl)ethyl group, 3-(2-pyridyl)propyl group, 3-(3-pyridyl)propyl group, 3-(4-pyridyl)propyl group, 2-pyrazylmethyl group, 3-pyrazylmethyl group, 2-(2-pyrazyl)ethyl group, 2-(3-pyrazyl)ethyl group, 3-(2-pyrazyl)propyl group, 3-(3-pyrazyl)propyl group, 2-pyrimidylmethyl group, 4-pyrimidylmethyl group, 2-(2-pyrimidyl)ethyl group, 2-(4-pyrimidyl)ethyl group, 3-(2-pyrimidyl)propyl group, 3-(4-pyrimidyl)propyl group, 2-furylmethyl group, 3-furylmethyl group, 2-(2-furyl)ethyl group, 2-(3-furyl)ethyl group, 3-(2-furyl)propyl group and 3-(3-furyl)propyl group. Among these, 5- to 10-membered heteroaryl C1-6 alkyl groups are preferable.

Examples of an aralkyloxy group include a benzyloxy group, phenethyloxy group, 3-phenylpropyloxy group, 1-naphthylmethyloxy group and 2-naphthylmethyloxy group.

Examples of heteroaralkyloxy groups include a pyridylmethyloxy group, pyridylethyloxy group, pyridylpropyloxy group, pyrazylmethyloxy group, pyrazylethyloxy group, pyrazylpropyloxy group, pyrimidylmethyloxy group, pyrimidylethyloxy group, pyrimidylpropyloxy group, furylmethyloxy group, furylethyloxy group and furylpropyloxy group.

Examples of halogen atoms include a fluorine atom, chlorine atom, bromine atom and iodine atom.

Specific examples of amine compounds represented by formula [1] include 2-aminopyridine, 2-amino-3-picoline, 2-amino-6-picoline, 2-amino-6-bromopyridine, 2-amino-6-chloropyridine, 2-amino-6-chloromethylpyridine, 2-amino-6-ethylpyridine, 2-amino-6-propylpyridine, and (1-methyl-1H-tetrazol-5-yl)-phenyl-methanone O-(6-amino-pyridin-2-ylmethyl)-oxime.

The phosgene equivalent used in the present invention forms phosgene by decomposing in a reaction system. Specific examples thereof include diphosgene and triphosgene. The phosgene or phosgene equivalent may be added to the reaction system after dissolving in an organic solvent, or may be blown into the reaction system as a gas. Furthermore, the phosgene gas used in the present invention includes not only gas containing phosgene, but also gas that contains a phosgene equivalent.

Specific examples of the organic base used in the present invention include tertiary amines such as trimethylamine, triethylamine or N,N-diisopropylethylamine, and pyridines that may be substituted with a lower alkyl group such as a methyl group or ethyl group. Among these, tertiary amines are preferable, and triethylamine or N,N-diisopropylethylamine is more preferable.

The amount of phosgene used from start to completion of the reaction is preferably 0.8 moles to 10 moles, more preferably 0.85 moles to 8.5 moles, even more preferably 0.9 moles to 7 moles, and particularly preferably 1 mole to 5 moles based on 1 mole of the primary or secondary amine compound used from start to completion of the reaction. The amount of the phosgene equivalent is made to be such that the amount of phosgene generated as a result of decomposition thereof is within the aforementioned ranges.

The amount of t-butanol used from start to completion of the reaction is preferably 1 mole to 20 moles, more preferably 1 mole to 15 moles, even more preferably 1 mole to 10 moles and particularly preferably 1 mole to 5 moles based on 1 mole of the primary or secondary amine compound used from start to completion of the reaction.

The amount of the organic base used from start to completion of the reaction is preferably 1 mole to 10 moles, more preferably 1 mole to 8.5 moles, even more preferably 1.25 moles to 7 moles and particularly preferably 1.5 moles to 5 moles based on 1 mole of the compound having the primary or secondary amino group used from start to completion of the reaction.

The reaction according to the present invention is preferably carried out in an organic solvent. Examples of organic solvents include esters such as ethyl acetate or methyl acetate; halogenated hydrocarbons such as chloroform, methylene chloride or carbon tetrachloride; ethers such as tetrahydrofuran; ketones such as acetone or methyl isobutyl ketone; and aromatic hydrocarbons such as toluene or chlorobenzene.

Among these, ethyl acetate, chloroform, methylene chloride, toluene and chlorobenzene are preferable, and at least one type selected from the group consisting of ethyl acetate, chloroform and chlorobenzene is preferable. In addition, the temperature from start to completion of the reaction is preferably 40° C. or lower and more preferably 20° C. or lower.

In the present invention, a primary or secondary amine compound or a primary or secondary ammonium salt is reacted with phosgene or a phosgene equivalent.

Examples of the production process of the present invention include (A) a process comprising the addition of a solution containing a primary or secondary amine compound and an organic base to a solution containing phosgene or a phosgene equivalent and t-butanol, (B) a process comprising the addition of a solution containing a primary or secondary amine compound, an organic base and t-butanol to a solution containing phosgene or a phosgene equivalent, (C) a process comprising the substantially simultaneous addition of a solution containing a primary or secondary amine compound, a solution containing an organic base and a solution containing phosgene or a phosgene equivalent to a solution containing t-butanol, (D) a process comprising the addition of a solution containing a primary or secondary amine compound and a solution containing an organic base to a solution containing t-butanol while blowing in phosgene gas or phosgene equivalent gas, (E) a process comprising the addition of a solution containing t-butanol, a primary or secondary amine compound and an organic base to a reaction solution while blowing in phosgene gas, and (F) a process comprising the addition of an organic base to a solution containing phosgene or a phosgene equivalent, t-butanol and a primary or secondary ammonium salt.

There are no particular limitations on the preparation methods of each of the solutions used in the aforementioned processes of (A) to (F).

In the aforementioned process of (C) or (D), a solution containing a primary or secondary amine compound and an organic base may be added instead of adding a solution containing a primary or secondary amine compound and a solution containing an organic base.

Furthermore, in the aforementioned process of (C), the solution containing phosgene or a phosgene equivalent is preferably not allowed to mix with the solution containing a primary or secondary amine compound prior to be added to the solution containing t-butanol.

In addition, in the aforementioned process of (D), blowing in of the phosgene gas is preferably initiated prior to addition of the solution containing a primary or secondary amine compound.

The primary or secondary ammonium salt used in the aforementioned process of (F) is a salt comprised of a primary or secondary amine compound and an inorganic acid such as hydrochloric acid, sulfuric acid or nitric acid; or an organic acid such as tartaric acid, maleic acid or citric acid. Among these, a hydrochloride is preferable. It is difficult to react a primary or secondary ammonium salt with phosgene or a phosgene equivalent. According to the process of (F), when an organic base is added, the primary or secondary ammonium salt is converted to a primary or secondary amine compound. The primary or secondary amine compound formed as a result of this conversion then reacts with the phosgene or phosgene equivalent.

The amount of the primary or secondary amine compound can be adjusted according to the balance between the addition rates of the solutions used in the aforementioned processes (A) to (E) and rates at which the primary or secondary amine compound is consumed by the reaction. If the addition rate is faster than the rate of consumption, there is a surplus of the primary or secondary amine compound in the reaction system, thereby facilitating the occurrence of side reactions. Thus, the addition rate is set so that the amount of free primary or secondary amine compound in the reaction system is preferably 0.31 moles/1 mole of phosgene molecules or less, more preferably 0.26 moles/1 mole of phosgene molecules or less, even more preferably 0.22 moles/1 mole of phosgene molecules or less, and particularly preferably 0.19 moles/1 mole of phosgene molecules or less.

When phosgene or a phosgene equivalent reacts with the primary or secondary amine compound, a carbamoyl chloride compound is formed, after which hydrogen chloride is eliminated resulting in the formation of an isocyanate compound. The organic base present in the reaction system captures the eliminated hydrogen chloride. The formed carbamoyl chloride compound or isocyanate compound reacts with t-butanol present in the reaction system resulting in the formation of a t-butoxycarbonylamine compound. In the present invention, since the amount of primary or secondary amine compound in the reaction system is low, it is difficult for the formed carbamoyl chloride compound or isocyanate compound to react with the primary or secondary amine compound. As a result, the formation of bis-urea compounds as a by-product is inhibited.

In this manner, the selectivity of the t-butoxycarbonylamine compound can be enhanced by reacting phosgene or a phosgene equivalent with a primary or secondary amine compound in a state in which there is only a small amount of the primary or secondary amine compound present in the reaction system.

EXAMPLES

The following provides a more detailed explanation of the present invention by indicating examples and comparative examples thereof. Furthermore, the present invention is not limited to the following examples.

Example 1

14.8 g (200 millimoles) of t-butanol and 29 ml of ethyl acetate were added to a reaction system followed by blowing in 9.9 g (100 millimoles) of phosgene. A mixed solution containing 5.48 g (50.7 millimoles) of 2-amino-6-picoline, 12.5 g (97.0 millimoles) of N,N-diisopropylethylamine and 32 mL of ethyl acetate was dropped into this solution over the course of 1.5 hours while holding the internal temperature at −15° C. to −5° C. Following completion of dropping, the solution was stirred for 1 hour. Next, 50 mL of water and 5.1 g of 28% sodium hydroxide were sequentially added while holding the internal temperature at 0° C. or lower. After separating the liquid, the aqueous phase was extracted with ethyl acetate. The organic phases were combined and mixed, and a portion of the organic phase was sampled and subjected to quantitative analysis by HPLC. The target (6-methyl-pyridin-2-yl)-carbamic acid tert-butyl ester was obtained at a yield of 89%. The yield of 1,3-bis-(6-methyl-pyridin-2-yl)-urea (urea compound) was 8%. Furthermore, the yield of the urea compound was based on the raw material 2-amino-6-picoline and was calculated using 2 molecules of 2-amino-6-picoline for 1 molecule of the urea compound (and was similarly calculated in the subsequent examples and comparative examples).

Example 2

462 ml of ethyl acetate were added to a reaction system and cooled to −15° C. followed by blowing in 114.4 g (1.16 moles) of phosgene over the course of 1.8 hours. A mixed solution containing 50.2 g (0.462 moles) a of 2-amino-6-picoline, 131.8 g (1.02 moles) of N,N-diisopropylethylamine, 85.7 g (1.16 moles) of t-butanol and 231 mL of ethyl acetate was then dropped into this phosgene solution over the course of 2.8 hours while holding the internal temperature at −15° C. to 0° C. Following completion of dropping, the solution was stirred for 1.7 hours. Next, 300 mL of water and 200 mL of 28% sodium hydroxide were sequentially added while holding the internal temperature at 0° C. or lower. The aqueous phase was extracted with 300 mL of ethyl acetate. The organic phases were combined and mixed and then concentrated under reduced pressure. A mixed solution of methanol and water was added to the resulting crude product. The precipitated crystals were then subjected to suction filtration and dried under reduced pressure to obtain 93.4 g of the target (6-methyl-pyridin-2-yl)-carbamic acid tert-butyl ester (yield: 94%). The yield of 1,3-bis-(6-methyl-pyridin-2-yl)-urea (urea compound) was 3%.

Example 3

55.6 g (0.75 moles) of t-butanol and 450 mL of chloroform were added to a reaction system followed by blowing in 65.3 g (0.66 moles) of phosgene over the course of 2.5 hours while holding the internal temperature at −5° C. to 0° C., and then simultaneously supplying a mixed solution containing 32.4 g (0.30 moles) of 2-amino-6-picoline, 133.5 g (1.32 moles) of triethylamine and 300 mL of chloroform to the reaction system over the course of 2.5 hours using a metering pump (supply rate: 3 mL/min). After supplying the mixed solution, the solution was stirred for 1 hour at 0° C. Next, water and 28% sodium hydroxide were sequentially added while holding the internal temperature at 0° C. or lower. After separating the liquid, the aqueous phase was extracted with chloroform, and the organic phases were combined and mixed. A portion of the organic phase was sampled and subjected to quantitative analysis by HPLC. The target (6-methyl-pyridin-2-yl)-carbamic acid tert-butyl ester was obtained at yield of 98%. Only an extremely small amount of 1,3-bis-(6-methyl-pyridin-2-yl)-urea (urea compound) was present.

Example 4

34 mL of ethyl acetate and 5.42 g (50.1 millimoles) of 2-amino-6-picoline were added to a reaction system followed by blowing in 2.2 g (60.3 millimoles) of hydrochloric acid gas to form a hydrochloride of 2-amino-6-picoline. 14.8 g (200 millimoles) of t-butanol were then added thereto followed by blowing in 10.0 g (101.1 millimoles) of phosgene over the course of 40 minutes while holding the internal temperature at −5° C. to −10° C. 19.5 g (150.7 millimoles) of N,N-diisopropylethylamine and an ethyl acetate solution (34 mL) were then dropped into this slurry solution over the course of 1.5 hours while holding the internal temperature at −5° C. to −10° C. Following completion of dropping, water and 28% sodium hydroxide were sequentially added while holding the internal temperature at 0° C. or lower. After separating the liquid, the aqueous phase was extracted with ethyl acetate, and the organic phases were combined and mixed. A portion of the organic phase was sampled and subjected to quantitative analysis by HPLC. The target (6-methyl-pyridin-2-yl)-carbamic acid tert-butyl ester was obtained at yield of 84%. The yield of 1,3-bis-(6-methyl-pyridin-2-yl)-urea (urea compound) was 14%.

Example 5

5.61 g (75.7 millimoles) of t-butanol and 22 mL of ethyl acetate were added to a reaction system followed by blowing in 3.8 g (38.4 millimoles) of phosgene. A mixed solution containing 1.95 g (13.7 millimoles) of 2-amino-6-chloromethylpyridine, 4.86 g (37.6 millimoles) of N,N-diisopropylethylamine and 19 mL of ethyl acetate were dropped into this solution over the course of 1 hour while holding the internal temperature at −15° C. to −5° C. Following completion of dropping, the solution was stirred for 1 hour. Next, water and 28% sodium hydroxide were sequentially added while holding the internal temperature at 0° C. or lower. After separating the liquid, the aqueous phase was extracted with ethyl acetate. The organic phases were combined and mixed. A portion of the organic phase was sampled and subjected to quantitative analysis by HPLC. The target (6-chloromethyl-pyridin-2-yl)-carbamic acid tert-butyl ester was obtained at yield of 74%. The yield of 1,3-bis-(6-chloromethyl-pyridin-2-yl)-urea (urea compound) was 10%.

Example 6

20 mL of ethyl acetate were added to a reaction system and cooled to about −15° C. followed by blowing in 1.19 g (12.0 millimoles) of phosgene. A mixed solution containing 1.31 g (purity: 95%, 4.0 millimoles) of (1-methyl-1H-tetrazol-5-yl)-phenyl-methanone O-(6-amino-pyridin-2-ylmethyl)-oxime, 1.04 g (8.0 millimoles) of N,N-diisopropylethylamine, 1.19 g (16.1 millimoles) of t-butanol and 60 mL of ethyl acetate were dropped into this phosgene solution over the course of 1.5 hours while holding the internal temperature at −15° C. to −5° C. Following completion of dropping, the solution was stirred for 3 hours at the same temperature range. Next, 20 mL of water and a small amount of 28% sodium hydroxide were sequentially added while holding the internal temperature at 0° C. or lower. The separated aqueous phase was extracted with ethyl acetate. The organic phase was washed with water. The organic phase was subjected to quantitative analysis by HPLC. The target {6-[1-(1-methyl-1H-tetrazol-5-yl)-1-phenyl-methylideneamino ximeethyl]-pyridin-2-yl}-carbamic acid tert-butyl ester was obtained at a yield of 88%. 9% of the (1-methyl-1H-tetrazol-5-yl)-phenyl-methanone O-(6-amino-pyridin-2-ylmethyl)-oxime used for the starting material remained. There was hardly any urea compound formed.

Example 7

87 mL of ethyl acetate were added to a reaction system and cooled to −15° C. followed by blowing in 14.3 g (144.5 millimoles) of phosgene. A mixed solution containing 10.0 g (57.8 millimoles) of 2-amino-6-bromopyridine, 14.9 g (115.6 millimoles) of N,N-diisopropylethylamine, 8.57 g (115.6 millimoles) of t-butanol and 58 mL of ethyl acetate were dropped into this phosgene solution over the course of 1.8 hours while holding the internal temperature at −15° C. to −5° C. Following completion of dropping, the solution was stirred for 1 hour at the same temperature range. Next, 60 mL of water and 39.6 g of 28% sodium hydroxide were sequentially added while holding the internal temperature at 0° C. or lower. The aqueous phase was extracted with ethyl acetate. The organic phase was washed with water and concentrated under reduced pressure. The resulting crude crystals were subjected to quantitative analysis by HPLC. The target (6-bromo-pyridin-2-yl)-carbamic acid tert-butyl ester was obtained at a yield of 81%. There was hardly any urea compound formed.

Example 8

64 mL of ethyl acetate were added to a reaction system and cooled to about −15° C. with a salt and ice bath followed by blowing in 10.6 g (107 millimoles) of phosgene. A mixed solution containing 5.5 g (42.8 millimoles) of 2-amino-6-chloropyridine, 11.1 g (85.6 millimoles) of N,N-diisopropylethylamine, 6.34 g (85.5 millimoles) of t-butanol and 43 mL of ethyl acetate were dropped into this phosgene solution over the course of 2.5 hours while holding the internal temperature at −15° C. to −5° C. Following completion of dropping, the solution was stirred for 3 hours at the same temperature range. Next, 50 mL of water and 23.2 g of 28% sodium hydroxide were sequentially added while holding the internal temperature at 0° C. or lower. The aqueous phase was extracted with ethyl acetate. The organic phase was washed with water and concentrated under reduced pressure. The resulting crude crystals were subjected to quantitative analysis by HPLC. The target (6-chloro-pyridin-2-yl)-carbamic acid tert-butyl ester was obtained at a yield of 93%. There was hardly any urea compound formed.

Example 9

295.7 g (199 mL) of chloroform were added to a reaction system and cooled to 0° C. followed by blowing in 43.08 g (0.436 moles) of phosgene over the course of 0.5 hours. A mixed solution containing 21.66 g (0.200 moles) of 2-amino-6-picoline, 20.26 g (0.200 moles) of triethylamine, 37.02 g (0.499 moles) of t-butanol and 89.6 g (60 mL) of chloroform were dropped into this phosgene solution over the course of 1.0 hours while holding the internal temperature at −3° C. to 2° C. Following completion of dropping, the solution was stirred for 1.4 hours. Next, 20.30 g (0.201 moles) of triethylamine and 59.4 g (40 mL) of chloroform were dropped in over the course of 0.8 hours while holding the internal temperature at 0° C. to 5° C. Following completion of dropping, the solution was stirred for 1.0 hours. Next, 122.5 g (82 mL) of chloroform were added. The reaction solution was subjected to quantitative analysis by HPLC. The target (6-methyl-pyridin-2-yl)-carbamic acid tert-butyl ester was obtained at a yield of 94%. The yield of 1,3-bis-(6-methyl-pyridin-2-yl)-urea (urea compound) was 2%.

Example 10

556.0 g (500 mL) of monochlorobenzene were added to a reaction system followed by blowing in 107.8 g (1.09 moles) of phosgene over the course of 1 hour at −10° C. to −5° C. A mixed solution containing 54.07 g (0.5 moles) of 2-amino-6-picoline, 107 g (1.06 moles) of triethylamine, 92.7 g (1.25 moles) of t-butanol and 333 g (300 mL) of monochlorobenzene were dropped into this phosgene solution over the course of 4.5 hours while holding the internal temperature at −11° C. to −8° C. Following completion of dropping, the solution was stirred for 0.5 hours. Next, a mixed solution obtained by dissolving 120 g (1.19 moles) of triethylamine in 217.4 g (200 mL) of monochlorobenzene was dropped in over the course of 1 hour while holding the internal temperature at −10° C. to −5° C. Following completion of dropping, the solution was stirred for 0.2 hours. Next, 300 mL of water were added. The organic phase was washed with 150 mL of water. The organic phase was subjected to quantitative analysis by HPLC. The target (6-methyl-pyridin-2-yl)-carbamic acid tert-butyl ester was obtained at a yield of 92%. The yield of 1,3-bis-(6-methyl-pyridin-2-yl)-urea (urea compound) was 4%. 4% of the 2-amino-6-picoline used for the starting material remained.

Example 11

1702 mL of chloroform were added to a reaction system and cooled to −15° C. followed by blowing in 218.60 g (2.21 moles) of phosgene over the course of 3.7 hours. A mixed solution containing 108.19 g (1.00 moles) of 2-amino-6-picoline, 101.13 g (1.00 moles) of triethylamine, 185.18 g (2.50 moles) of t-butanol and 295 mL of chloroform were dropped into this phosgene solution over the course of 2.8 hours while holding the internal temperature at −15° C. to −5° C. Following completion of dropping, the solution was stirred for 1.4 hours. Next, 343.7 g (3.40 moles) of triethylamine were dropped in over the course of 2.6 hours while holding the internal temperature at −15° C. to 2° C. Following completion of dropping, the solution was stirred for 0.2 hours. Next, 238 mL of water and 931 mL of 28% sodium hydroxide were added sequentially. The aqueous phase was extracted with 50 mL of chloroform. The organic phases were combined and subjected to quantitative analysis by HPLC. The target (6-methyl-pyridin-2-yl)-carbamic acid tert-butyl ester was obtained at a yield of 96%. The yield of 1,3-bis-(6-methyl-pyridin-2-yl)-urea (urea compound) was 3%.

Comparative Example 1

100 mL of ethyl acetate were added to a reaction system and cooled to about −15° C. followed by blowing in 24.7 g (0.25 moles) of phosgene over the course of 0.3 hours. A mixed solution containing 11.0 g (0.102 moles) of 2-amino-6-picoline, 71.3 g (0.552 moles) of N,N-diisopropylethylamine and 20 mL of ethyl acetate were dropped into this phosgene solution over the course of 1.5 hours while holding the internal temperature at −15° C. to −5° C. Following completion of dropping, the solution was stirred for 30 minutes at the same temperature range. Next, an ethyl acetate solution (30 mL) of 11.1 g (0.15 moles) of t-butanol was added and stirred for 4 hours following completion of addition. Next, water and 28% sodium hydroxide were sequentially added while holding the internal temperature at 0° C. or lower. After separating the liquid, the aqueous phase was extracted with ethyl acetate. The organic phases were combined and mixed. A portion of the organic phase was sampled and subjected to quantitative analysis by HPLC. A large amount of numerous types of impurities formed. The yield of the target (6-methyl-pyridin-2-yl)-carbamic acid tert-butyl ester was 20%, and the yield of 1,3-bis-(6-methyl-pyridin-2-yl)-urea (urea compound) was 20%.

Comparative Example 2

14.8 g (200 millimoles) of t-butanol, 67 mL of ethyl acetate, 12.9 g (100 millimoles) of N,N-diisopropylethylamine and 5.41 g (50 millimoles) of 2-amino-6-picoline were added to a reaction system followed by blowing in 9.1 g (92.0 millimoles) of phosgene over the course of 1 hour while holding the internal temperature at −5° C. to 0° C. Following completion of blowing, the solution was stirred for 2.5 hours. Next, water and 28% sodium hydroxide were sequentially added while holding the internal temperature at 0° C. or lower. After separating the liquid, the aqueous phase was extracted with ethyl acetate. The organic phases were combined and mixed. A portion of the organic phase was sampled and subjected to quantitative analysis by HPLC. The yield of 1,3-bis-(6-methyl-pyridin-2-yl)-urea (urea compound) was 47% and a remarkably large amount was formed. The yield of the target (6-methyl-pyridin-2-yl)-carbamic acid tert-butyl ester was 47%.

Comparative Example 3

34 mL of ethyl acetate and 5.41 g (50.0 millimoles) of 2-amino-6-picoline were added to a reaction system followed by blowing in 3.6 g (98.7 millimoles) of hydrochloric acid gas to form a hydrochloride of 2-amino-6-picoline. 14.8 g (200 millimoles) of t-butanol were added thereto followed by blowing in 14.0 g (141.5 millimoles) of phosgene over the course of 1.7 hours while holding the internal temperature at −5° C. to −10° C. Following completion of blowing, the solution was stirred for 1.5 hours at the same temperature range. Residual phosgene was removed by blowing in nitrogen gas. Subsequently, water and 28% sodium hydroxide were sequentially added while holding the internal temperature at 0° C. or lower. After separating the liquid, the aqueous phase was extracted with ethyl acetate. The organic phases were combined and mixed. A portion of the organic phase was sampled and subjected to quantitative analysis by HPLC. 66% of the starting 2-amino-6-picoline remained. The yield of the target (6-methyl-pyridin-2-yl)-carbamic acid tert-butyl ester was 13%. The yield of 1,3-bis-(6-methyl-pyridin-2-yl)-urea (urea compound) was 4%.

Comparative Example 4

1.08 g (10 millimoles) of 2-amino-6-picoline, ethyl acetate (30 mL, 3 L/mol), 5.17 g (40 millimoles) of diisopropylethylamine and 2.37 g (8 millimoles, 0.8 times moles) of triphosgene were added to a reaction system followed by stirring for 2 hours at 50° C. 10 mL (1 L/mol) of t-butanol were added to this solution followed by stirring for 2 hours at 50° C. Water and 28% sodium hydroxide were sequentially added while holding the internal temperature at 0° C. or lower. After separating the liquid, the aqueous phase was extracted with ethyl acetate. The organic phases were combined and mixed. A portion of the organic phase was sampled and subjected to quantitative analysis by HPLC. The yield of the target (6-methyl-pyridin-2-yl)-carbamic acid tert-butyl ester was 46%. The yield of 1,3-bis-(6-methyl-pyridin-2-yl)-urea (urea compound) was 31% and was formed secondarily in the reaction in a large amount.

Comparative Example 5

2.43 g (10 millimoles) of 2-amino-6-chloromethylpyridine, ethyl acetate (30 mL), 3.88 g (30 millimoles) of N,N-diisopropylethylamine and 1.48 g (5 millimoles) of triphosgene were added to a reaction system followed by stirring for 1 hour at 60° C. 10 mL of t-butanol were added to this solution followed by stirring for 1 hour at 60° C. Water and 28% sodium hydroxide were sequentially added while holding the internal temperature at 0° C. or lower. After separating the liquid, the aqueous phase was extracted with ethyl acetate. The organic phases were combined and mixed. A portion of the organic phase was sampled and subjected to quantitative analysis by HPLC. The yield of the target (6-chloromethyl-pyridin-2-yl)-carbamic acid tert-butyl ester was 41%. The yield of 1,3-bis-(6-chloromethyl-pyridin-2-yl)-urea (urea compound) was 60% and was formed secondarily in the reaction in a large amount.

Comparative Example 6

2.43 g (10 millimoles) of 2-amino-6-chloromethylpyridine, toluene (30 mL), 10 mL of t-butyl alcohol and 1.48 g (5 millimoles) of triphosgene were added to a reaction system followed by refluxing for 1 hour. Water and 28% sodium hydroxide were sequentially added while holding the internal temperature at 0° C. or lower. After separating the liquid, the aqueous phase was extracted with ethyl acetate. The organic phases were combined and mixed. A portion of the organic phase was sampled and subjected to quantitative analysis by HPLC. The target (6-chloromethyl-pyridin-2-yl)-carbamic acid tert-butyl ester was not formed at all. 1,3-bis-(6-chloromethyl-pyridin-2-yl)-urea (urea compound) constituted the main product.

Comparative Example 7

2.05 g (5 millimoles) of (1-methyl-1H-tetrazol-5-yl)phenyl-methanone O-(6-amino-pyridin-2-ylmethyl)-oxime, ethyl acetate (35 mL, 7 L/mol), 3.88 g (30 millimoles, 6 times moles) of N,N-diisopropylethylamine and 1.19 g (4 millimoles) of triphosgene were added to a reaction system followed by stirring for 1 hour at 50° C. 5 mL of t-butanol were added to this solution followed by stirring for 1 hour at 50° C. Water and 28% sodium hydroxide were sequentially added while holding the internal temperature at 0° C. or lower. After separating the liquid, the aqueous phase was extracted with ethyl acetate. The organic phases were combined and mixed. A portion of the organic phase was sampled and subjected to quantitative analysis by HPLC. The target {6-[1-(1-methyl-1H-tetrazol-5-yl)-1-phenyl-methylideneaminoximeethyl]-pyridin-2-yl}-carbamic acid tert-butyl ester was not formed at all. The yield of 1,3-bis-{6-[1-(1-methyl-1H-tetrazol-5-yl)-1-phenyl-methylideneaminoximeethyl]-pyridin-2-yl}-urea (urea compound) was 67% and was formed secondarily in the reaction in a large amount.

Industrial Applicability

According to the production process of the present invention, since a Boc group can be introduced into a primary or secondary amine compound inexpensively while inhibiting the formation of by-products, the present invention is extremely industrially useful.

The invention claimed is:

1. A process for producing a t-butoxycarbonylamine compound comprising the use of phosgene or a phosgene equivalent, t-butanol, an organic base and a primary or secondary amine compound or primary or secondary ammonium salt, which includes any one of following processes (a) to (f):
   (a) a process comprising the addition of a solution containing a primary or secondary amine compound and an organic base to a solution containing phosgene or a phosgene equivalent and t-butanol;
   (b) a process comprising the addition of a solution containing a primary or secondary amine compound, an organic base and t-butanol to a solution containing phosgene or a phosgene equivalent;
   (c) a process comprising a substantially simultaneous addition of a solution containing a primary or secondary amine compound, a solution containing an organic base and a solution containing phosgene or a phosgene equivalent to a solution containing t-butanol;
   (d) a process comprising the addition of a solution containing a primary or secondary amine compound and a solution containing an organic base to a solution containing t-butanol while blowing in phosgene gas;
   (e) a process comprising the addition of a solution containing t-butanol, a primary or secondary amine compound and an organic base to a reaction solution while blowing in phosgene gas; and,
   (f) a process comprising the addition of an organic base to a solution containing phosgene or a phosgene equivalent, t-butanol and a primary or secondary ammonium salt.

2. The process for producing a t-butoxycarbonylamine compound according to claim 1, wherein the primary or secondary ammonium salt is a primary or secondary ammonium hydrochloride.

3. The process for producing a t-butoxycarbonylamine compound according to claim 1, wherein the reaction is carried out in an organic solvent.

4. The process for producing a t-butoxycarbonylamine compound according to claim 3, wherein the organic solvent is at least one type selected from a group consisting of ethyl acetate, chlorobenzene and chloroform.

5. The process for producing a t-butoxycarbonylamine compound according to claim 2, wherein the reaction is carried out in an organic solvent.

6. The process for producing a t-butoxycarbonylamine compound according to claim 5, wherein the organic solvent is at least one type selected from a group consisting of ethyl acetate, chlorobenzene and chloroform.

7. The process for producing a t-butoxycarbonylamine compound according to any one of claims 1, 2, 3, 4, 5 or 6, wherein the primary or secondary amine compound is an amine compound having an N-substituted heteroaromatic hydrocarbon group.

8. The process for producing a t-butoxycarbonylamine compound according to claim 7, wherein the amine compound having an N-substituted heteroaromatic hydrocarbon group is a 2-aminopyridine derivative.

9. The process for producing a t-butoxycarbonylamine compound according to any one of claims 1, 2, 3, 4, 5 or 6, wherein the organic base is a tertiary amine.

10. The process for producing a t-butoxycarbonylamine compound according to claim 9, wherein the tertiary amine is N,N-diisopropylethylamine or triethylamine.

11. The process for producing a t-butoxycarbonylamine compounds according to any one of claims 1, 2, 3, 4, or 5, wherein the temperature from start of the reaction to completion of the reaction is 40° C. or lower.

12. The process for producing a t-butoxycarbonylamine compound according to claim 7, wherein the organic base is a tertiary amine.

13. The process for producing a t-butoxycarbonylamine compound according to claim 12, wherein the tertiary amine is N,N-diisopropylethylamine or triethylamine.

14. The process for producing a t-butoxycarbonylamine compound according to claim 13, wherein the temperature from start of the reaction to completion of the reaction is 40° C. or lower.

* * * * *